(12) United States Patent
Blusch

(10) Patent No.: US 6,251,637 B1
(45) Date of Patent: Jun. 26, 2001

(54) USE OF EXTREMELY THERMOPHILIC DNA-POLYMERASES

(75) Inventor: Juergen Blusch, Munich (DE)

(73) Assignee: GSF Forschungszentrum fuer Umwelt und Gesundheit GmbH, Neuherberg (DE)

( * ) Notice: Subject to any disclaimer, the term of this patent is extended or adjusted under 35 U.S.C. 154(b) by 0 days.

(21) Appl. No.: 09/155,512

(22) PCT Filed: Mar. 27, 1997

(86) PCT No.: PCT/EP97/01589

§ 371 Date: Apr. 7, 1999

§ 102(e) Date: Apr. 7, 1999

(87) PCT Pub. No.: WO97/37039

PCT Pub. Date: Oct. 9, 1997

(30) Foreign Application Priority Data

Mar. 29, 1996 (DE) .............................................. 196 12 684

(51) Int. Cl.[7] .............................. C12Q 1/68; C12P 19/34; C07H 21/02; C12N 15/00

(52) U.S. Cl. ................. 435/91; 435/6; 435/91.2; 536/23.1; 935/97

(58) Field of Search ........................... 435/6, 91.2, 91.1; 536/23.1; 935/77

(56) References Cited

U.S. PATENT DOCUMENTS 4,782,137 * 11/1988 Hopp et al. ........................... 530/328
5,614,365 * 3/1997 Tabor et al. .............................. 435/6

FOREIGN PATENT DOCUMENTS 0 655 506 A1 * 5/1995 (EP) ................................ C12Q/1/68

* cited by examiner

*Primary Examiner*—W. Gary Jones
*Assistant Examiner*—Joyce Tung
(74) *Attorney, Agent, or Firm*—Townsend and Townsend and Crew LLP

(57) ABSTRACT

Cycle sequencing of DNA with marker-labeled dideoxynucleotides is performed using extremely thermophilic DNA polymerases in a one-lane technique in which dideoxynucleotides labeled with a dye as a marker are used to obtain sequence ladders of more 500 bases. Chain elongation is performed at a temperature of 65 to 75° C. Surprisingly, it was found that chain elongation temperatures of substantially more than 60° C. could be used in cycle sequencing of DNA with marker labeled dye dideoxynucleotides when using extremely thermophilic DNA polymerases.

8 Claims, 11 Drawing Sheets

(11 of 11 Drawing Sheet(s) Filed in Color)

```
                          SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:1:

CAGCTATGAC CATGATTACG CC                                              22
```

US 6,251,637 B1

USE OF EXTREMELY THERMOPHILIC DNA-POLYMERASES

BACKGROUND OF THE INVENTION

1. Field of the Invention

The present invention is directed to a method for cycle sequencing of DNA with marker-substituted dideoxynucleotides using extremely thermophilic DNA polymerases as well as a novel use of extremely thermophilic DNA polymerases.

2. Description of the Prior Art

Sequence analysis of DNA has become an irretrievable tool both for basic research and for laboratory diagnostics and is used routinely. Sequencing protocols are almost exclusively based on the chain termination method of Sanger using radiolabeled or fluorescent markers for the labeling of DNA chains. Various companies are offering a plurality of different sequencing protocols. In particular, the protocol of Applied Biosystems company (ABI) for non-radioactive sequencing using dye-labeled dideoxy terminators (dye-dideoxy terminators) has been widely used.

If sequencing is performed using dye-dideoxy terminators, the DNA polymerases copy the DNA template to be sequenced in a primer-dependent manner. Chain termination is accomplished by incorporation of ddNTPs each labeled by a different fluorescent dye. This method enables the separation of the DNA sequence in a single lane whereas the classical DNA sequencing method of Sanger using unlabeled ddNTPs and performing the labeling of the chains by radioactive α-dATP or fluorescent primers requires a four-lane system and, in the case of one-lane analysis, an elaborate 4-primer method.

If the sequencing reaction is effected in a single cycle at 37° C. generally thermolabile polymerases are used such as the T7 DNA polymerase. For many applications this protocol provides excellent results; however, it has the disadvantage that it requires high amounts of template DNA (about 5 μg of plasmid DNA per reaction). This disadvantage is particularly recognized in the direct sequencing of PCR products. Insurmountable difficulties are frequently encountered if GC-rich templates are sequenced. In contrast, less than ⅕ of the template DNA is necessary in cycle sequencing using DNA polymerases obtained from extremely thermophilic organisms. This method comprises various cycles of denaturation, annealing of the sequencing primer and chain elongation with subsequent ddNTP incorporation. According to the prior art this latter step has been carried out at 60° C. which in the case of the sequencing of GC-rich DNA sequences and of DNA having secondary structures leads to superior results over the protocols using only a single cycle at 37° C. However, the temperature of 60° C. used in the protocols according to the prior art is far below the optimum synthesis temperature of extremely thermostable DNA polymerases.

Unlike the protocol mentioned above, dye primer protocols are able to use an optimum chain elongation temperature of 72° C. However, these protocols require a cost-intensive extra-synthesis of fluorescence-labeled primers: of 1 primer in the case of the 4-lane method, and even of 4 primers if the 1-lane analysis is performed. While dye terminator sequencing is carried out in only one sample, in both of the cases the preparation of 4 parallel reactions is necessary each containing one of the ddNTPs leading to an additional increase in time and costs.

Protocols for dye primer sequencing are described by various companies for different extremely thermostable DNA polymerases. Examples for such protocols are those of ABI/Perkin Elmer, using AmpliTaq® and AmpliTaqFS®, Amersham using Thermosequenase® or of Epicentre using Sequitherm® DNA polymerase.

If the dye primer sequencing is used as a 1-lane technique it is necessary to provide four different primers with different dye labels. However, this accordingly leads to an increase in the time and costs required for sequencing.

Up to now successful cycle sequencing using dye terminators is known from the prior art only at a chain elongation temperature of 60° C., and this has been applied to the AmpliTaq®, AmpliTaqFS®, Thermosequenase®, Sequitherm®, and Tfl DNA polymerase enzymes. To date no protocols have been reported for temperatures in excess of 60° C. for cycle sequencing using dye terminators.

SUMMARY OF THE INVENTION

It is an object of the present invention to provide a novel method for cycle sequencing of DNA using dye terminators which may be used also on GC-rich sequences and which is usable at or near the optimum chain elongation temperature.

According to the invention this object has been solved by the addition of additives for the stimulation of primer annealing, chain elongation and DNA polymerase activity.

Furthermore, the present invention provides a novel use of extremely thermostable DNA polymerases. Preferred embodiments are characterized in more detail in the dependent claims.

BRIEF DESCRIPTION OF THE DRAWINGS

The file of this patent contains at least one drawing executed in color. Copies of this patent with color drawings are provided to the Patent and Trademark Office with payment of the necessary fee.

DETAILED DESCRIPTION OF THE PREFERRED INVENTION

Figure 1:
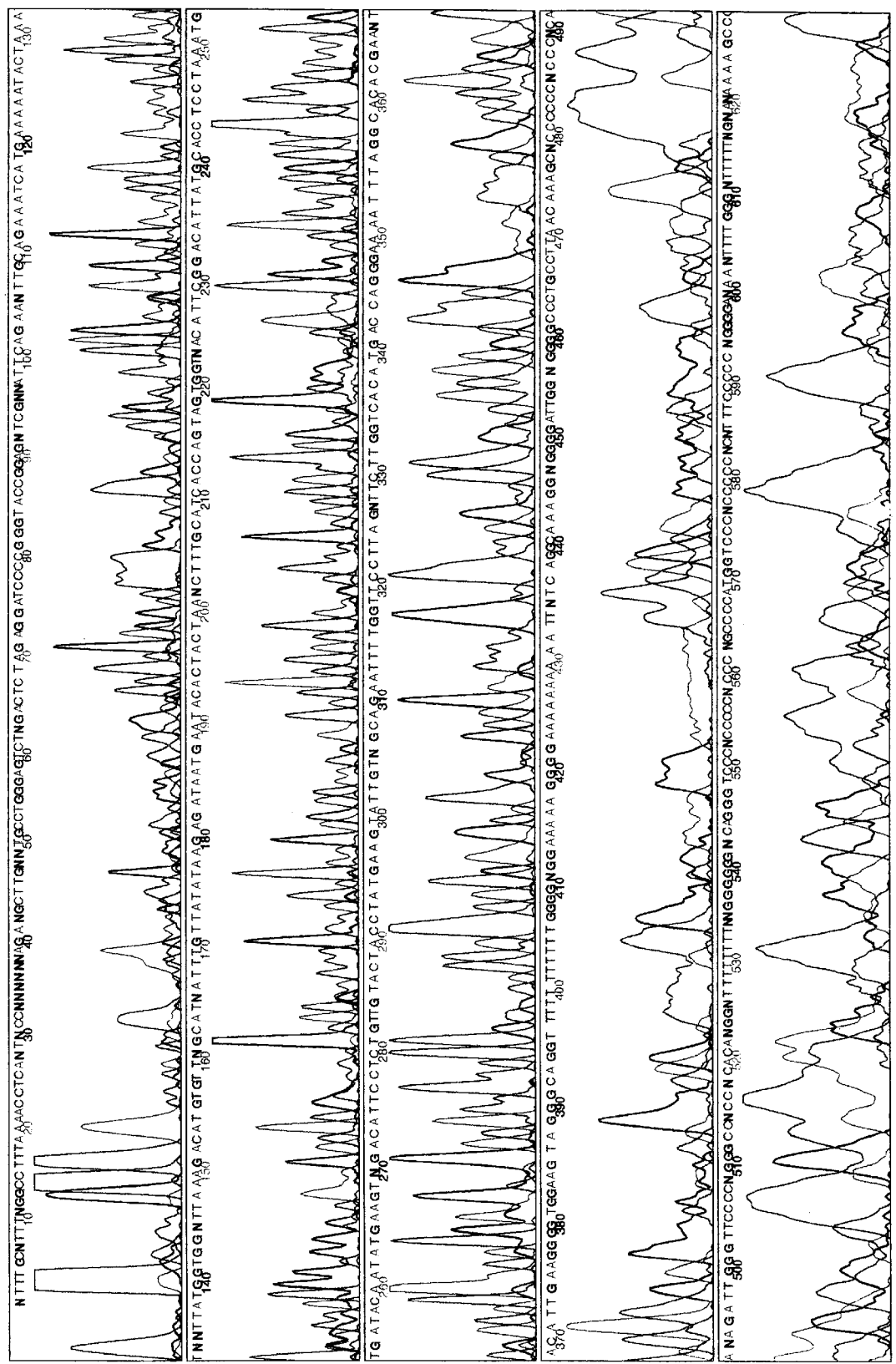
FIG. 1 is a sequencing readout of cycle sequencing in accordance with this invention, obtained using Sequitherm® DNA Polymerase.

The extremely thermostable DNA polymerases useful according to the invention are DNA deoxynucleotidyl transferases, E.C.2.7.7.7. Preferably, the following extremely thermostable DNA polymerases may be used:

AmpliTaq® (Perkin Elmer): strain *Thermus aquaticus* YT1;

Taq® DNA polymerase (Gibco): isolated from *Thermus aquaticus* strain YT1;

Sequitherm® DNA polymerase (Epicentre): DNA polymerase specifically developed for cycle sequencing;

Tth DNA polymerase (Epicentre): isolated from *Thermus thermophilus*;

Tth DNA polymerase (Boehringer): E.C.2.7.7.7., isolated from *Thermus thermophilus* HB8;

Expand® High Fidelity (Boehringer): mixture of Taq® and Pwo® DNA polymerases, E.C.2.7.7.7.;

Pwo® DNA polymerase (Boehringer): E.C.2.7.7.7., from *Pyrococcus woesei*;

Deep Vent® DNA polymerase (New England Biolabs): DNA polymerase gene from Pyrococcus species, isolate GB-D, expressed in *E. coli*;

9°N DNA polymerase (New England Biolabs): Thermococcus species, strain 9°N-7;

Vent® exo$^{31}$ DNA polymerase (New England Biolabs) : exo$^-$ DNA polymerase gene from *Thermococcus litoralis* expressed in *E. coli*;

Replitherm® DNA polymerase (Epicentre): not from *Thermus aquaticus*;

Goldstar® (Eurogentec): DNA polymerase gene from a new Thermus species expressed in *E. coli*;

Tfl DNA polymerase (Epicentre): isolated from *Thermus flavus*;

Pfu DNA polymerase (Stratagene): from *Pyrococcus furiosus* expressed in *E. coli*, strong 3'–5' exonuclease;

Thermosequenase® (Amersham): extremely thermostable DNA polymerase specifically developed for cycle sequencing;

AmpliTaq FS® (Perkin Elmer): mutated form of AmpliTaq® DNA polymerase lacking 5'–3' exonuclease.

Particularly preferred according to the invention are Sequitherm® and Tth DNA polymerases. The advantages of the use of these polymerases in cycle sequencing using dye terminators include the following:

less template DNA required as compared to the AmpliTaq® DNA polymerase protocol of ABI;

lower enzyme costs by reducing the amount of enzyme;

shorter reaction times and thereby increased sample processing;

elevated synthesis temperature up to 75° C. thereby enabling to work with higher specificity and at an "optimal" denaturation of the template DNA;

improved utilization of the sequencing chemicals and thus lowering the costs.

It is known from the prior art that extremely GC rich sequences sometimes may not be amplified in the PCR and are even less accessible to sequence analysis. In this context the difference in chain elongation temperature between PCR and cycle sequencing gained importance in experimentation. While in the frame of a research project a specific region from the human S71 locus could be amplified in PCR the resulting fragments could not be sequenced. The reason obviously was the chain elongation temperature which in the case of PCR is 72° C. but is 60° C. in cycle sequencing. The thermostability of certain DNA sequences may be experimentally reduced by replacing G and C bases by the analogs 7-deaza G and 5-methyl C showing less strong interactions. The approach to prepare fragments by PCR in which all of the G and C positions were replaced by analogs failed because of the incorporation of 7-deaza dGTP. However, protocols including the Sequitherm DNA polymerase protocol use this G analog in non-dye-terminator reactions as the only G component at a chain elongation temperature of 72° C. in order to suppress compressions on sequencing gels.

Therefore, it was attempted according to the invention to incorporate the dye terminators at elevated chain elongation temperatures, i.e. temperatures >60° C., initially selecting the Sequitherm® DNA polymerase as an example.

In the following the invention will be illustrated in more detail with reference to the FIGS. : The FIGS. show:

FIG. 1

Optimized Protocol for Cycle Sequencing With Sequitherm® DNA Polymerase

Sequences of more than 500 bases were achieved with Sequitherm® DNA polymerase for the pS71JB/"β-gal forward" standard primer/template pair after improving the dNTP/dyeddNTP ratio at a chain elongation temperature of 72° C. for 2 minutes. Per 21 μl final volume were combined: 0.5 μg of template, 10 pmoles primer, 2 μl 5×TACS buffer, 1 μl 30 mM MgCl$_2$, 0.1 μl 6 mM dITP/2 mM each of dATP/dTTP/dCTP/dGTP, 1 μl ABI nucleotide mix, 0.5 μl each of dyeddA/dyeddG/dyeddT, 0.25 μl dyeddc, 2.5 U enzyme and water up to a final volume of 21 μl. The SeqT580 PCR protocol was used at elongation conditions of 72° C. for 2 minutes.

FIG. 2

Optimized Protocol for Cycle Sequencing With Tth DNA Polymerase

Sequences of more than 500 bases were achieved with Tth DNA polymerase for the pS71JB/"β-gal forward" standard primer/template pair at a chain elongation temperature of 72° C. for 2 minutes. Per 21 μl final volume were combined: 0.5 μg of template, 10 pmoles primer, 4 μl 5×TACS buffer, 1 μl 30 mM MgCl$_2$, 2 μl each of 500 μM dITP/dATP/dTTP/dCTP/ 100 μM dGTP, 1 μl ABI nucleotide mix, 0.5 μl each of dyeddA/dyeddG, 0.25 μl dyeddc, 2.5 U enzyme and water up to a final volume of 21 μl. As in the case of Sequitherm® DNA polymerase the SeqT580 PCR protocol was modified to elongation conditions of 72° C. for 2 minutes.

Figure 3A:
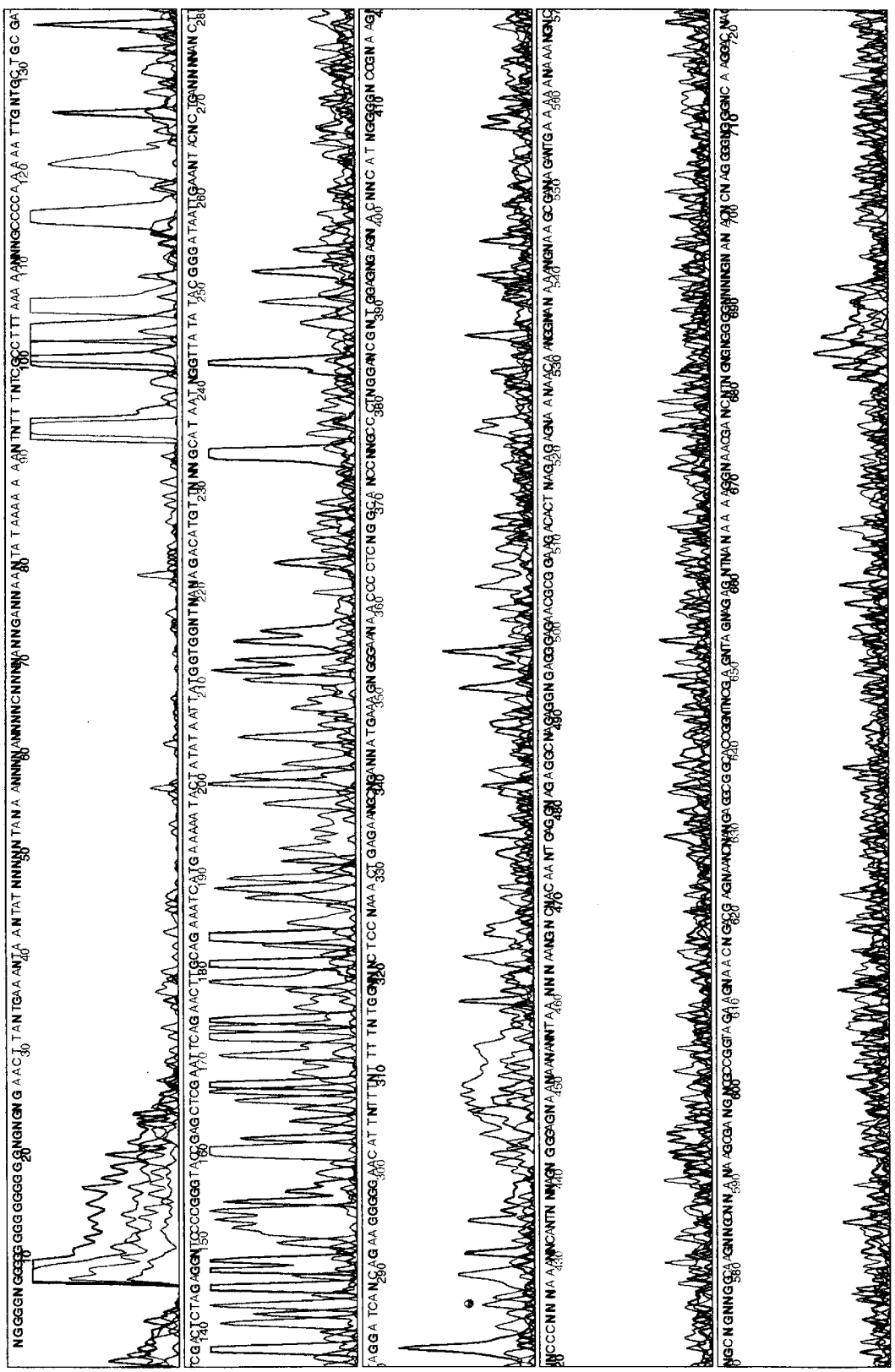
FIGS. 3a and 3b are sequencing readouts of cycle sequencing in accordance with this invention, obtained using Replitherm® DNA polymerase without the addition of magnesium (3a) and with the addition of magnesium (3b).
Figure 3B:
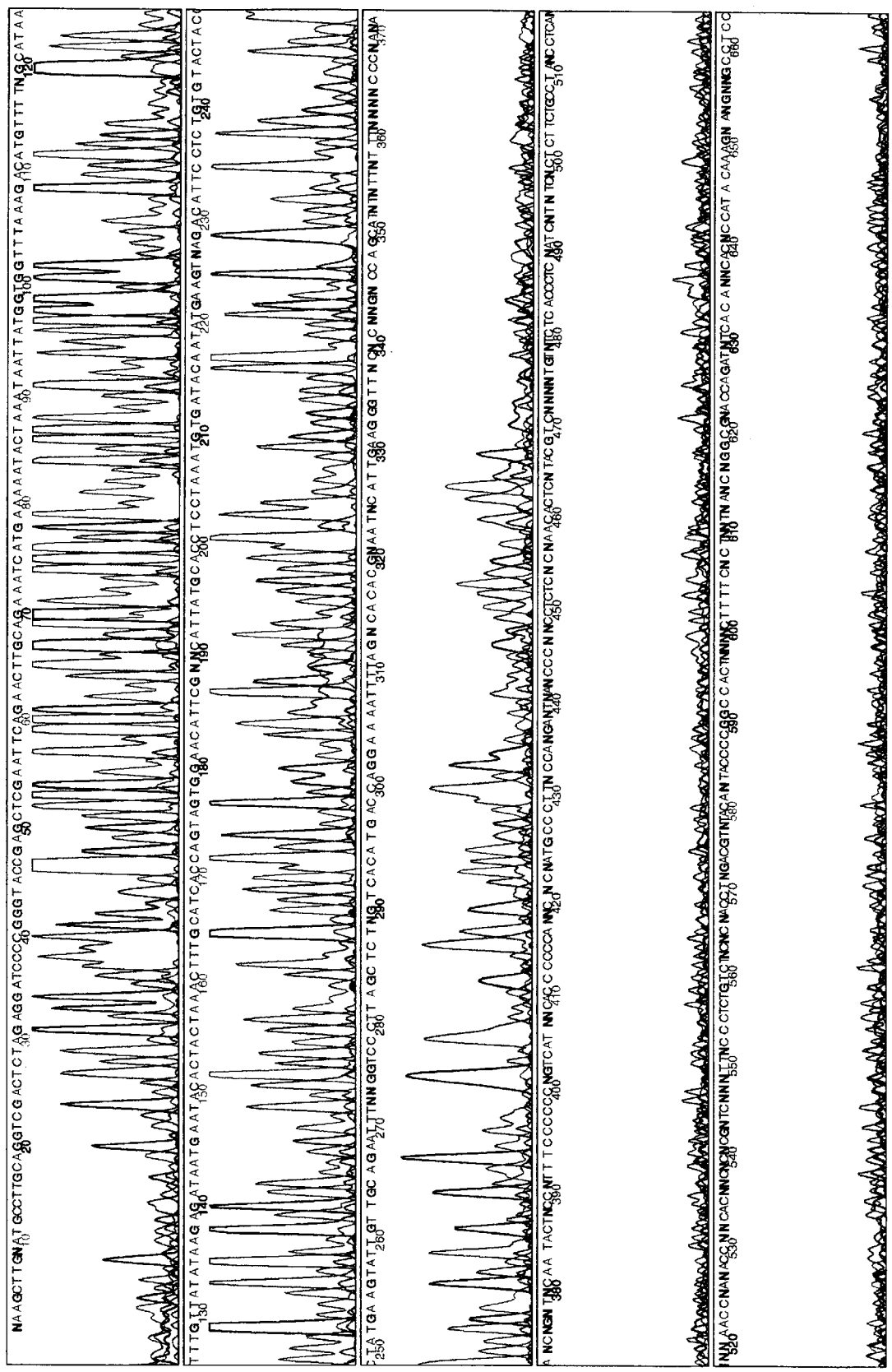

FIGS. 3a and 3b

Standard Cycle Sequencing Without (a) and With (b) Addition of Magnesium Using Replitherm® DNA Polymerase as an Example Using the standard conditions determined (0.5 μg of template, 10 pmoles primer, ½ ABI premix, 0.5 μl each of 500 μM dITP/dATP/dTTP/dCTP/100 μM dGTP, 2.5 U enzyme, water up to a final volume of 21 μl, SeqT580 PCR protocol with an elongation temperature of 70° C.) Replitherm® DNA polymerase was tested without (a) and with (b) addition of 1 μl 30 mM MgCl$_2$ for the pS71JB1/"β-gal forward" standard primer/template pair.

Figure 4A:
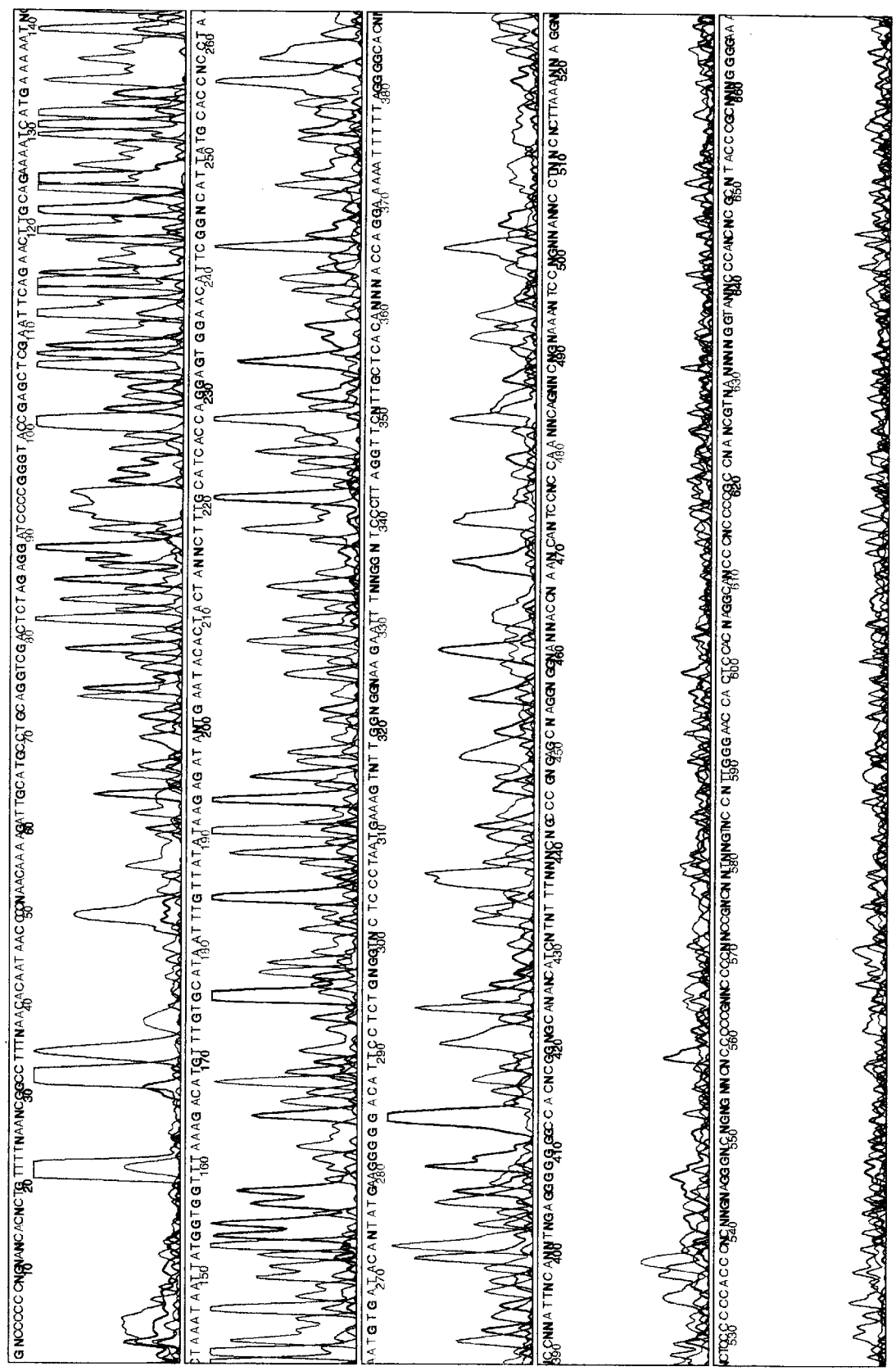
FIGS. 4a and 4b are sequencing readouts of cycle sequencing in accordance with this invention, obtained using Tfl DNA polymerase without the addition of magnesium (4a) and with the addition of magnesium (4b).
Figure 4B:
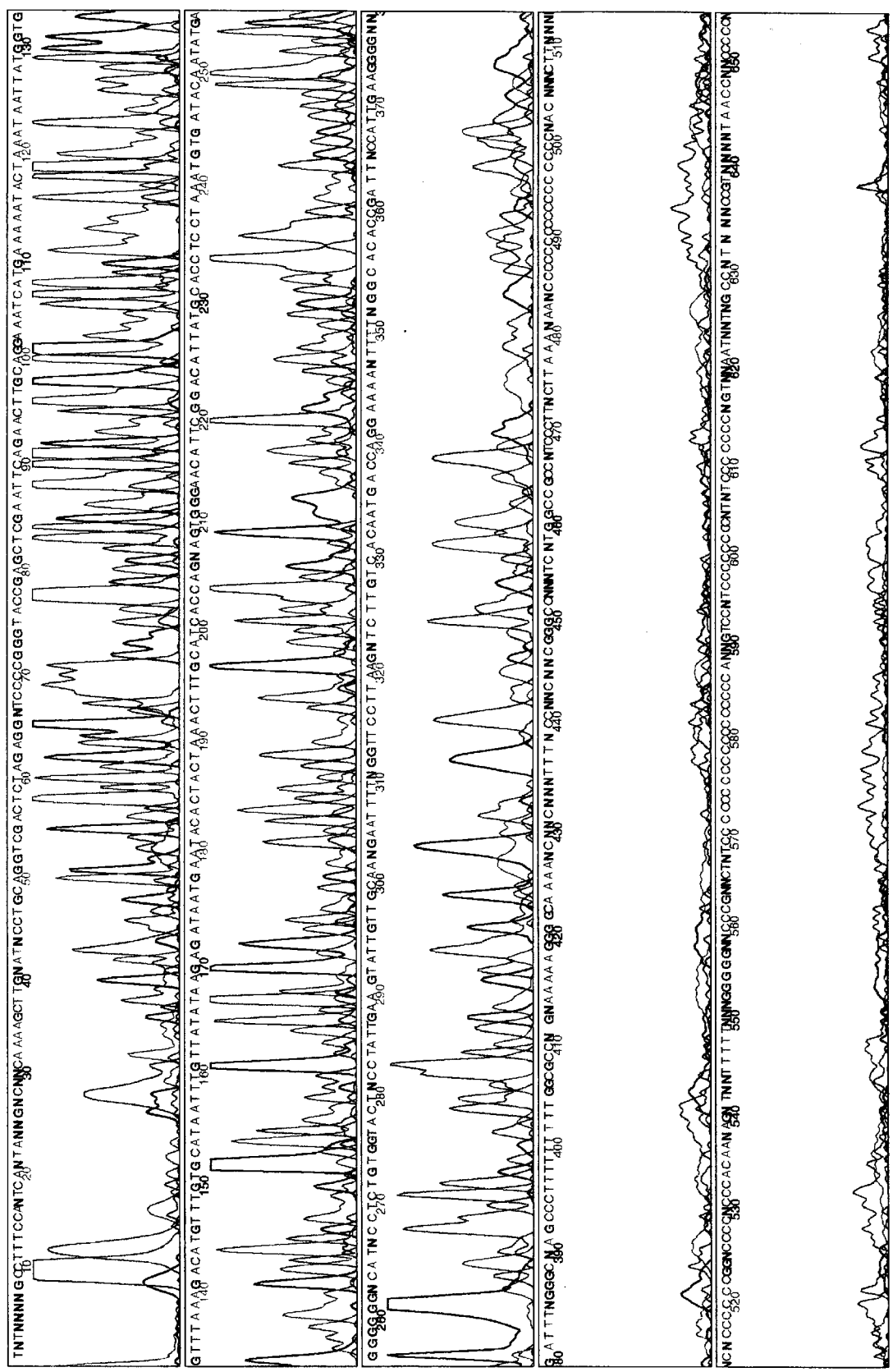

FIGS. 4a and 4b

Standard Cycle Sequencing Without (a) and with (b) Addition of Magnesium Using Tfl DNA Polymerase as an Example Using the standard conditions determined (0.5 μg of template, 10 pmoles primer, ½ ABI premix, 0.5 μl each of 500 μM dITP/dATP/dTTP/dCTP/100 μM dGTP, 2.5 U enzyme, water up to a final volume of 21 μl, SeqT580 PCR protocol with an elongation temperature of 70° C.) Tfl DNA polymerase was tested without (a) and with (b) addition of 1 μl 30 mM MgCl$_2$ for the pS71JB1/"β-gal forward" standard primer/template pair.

Figure 5A:
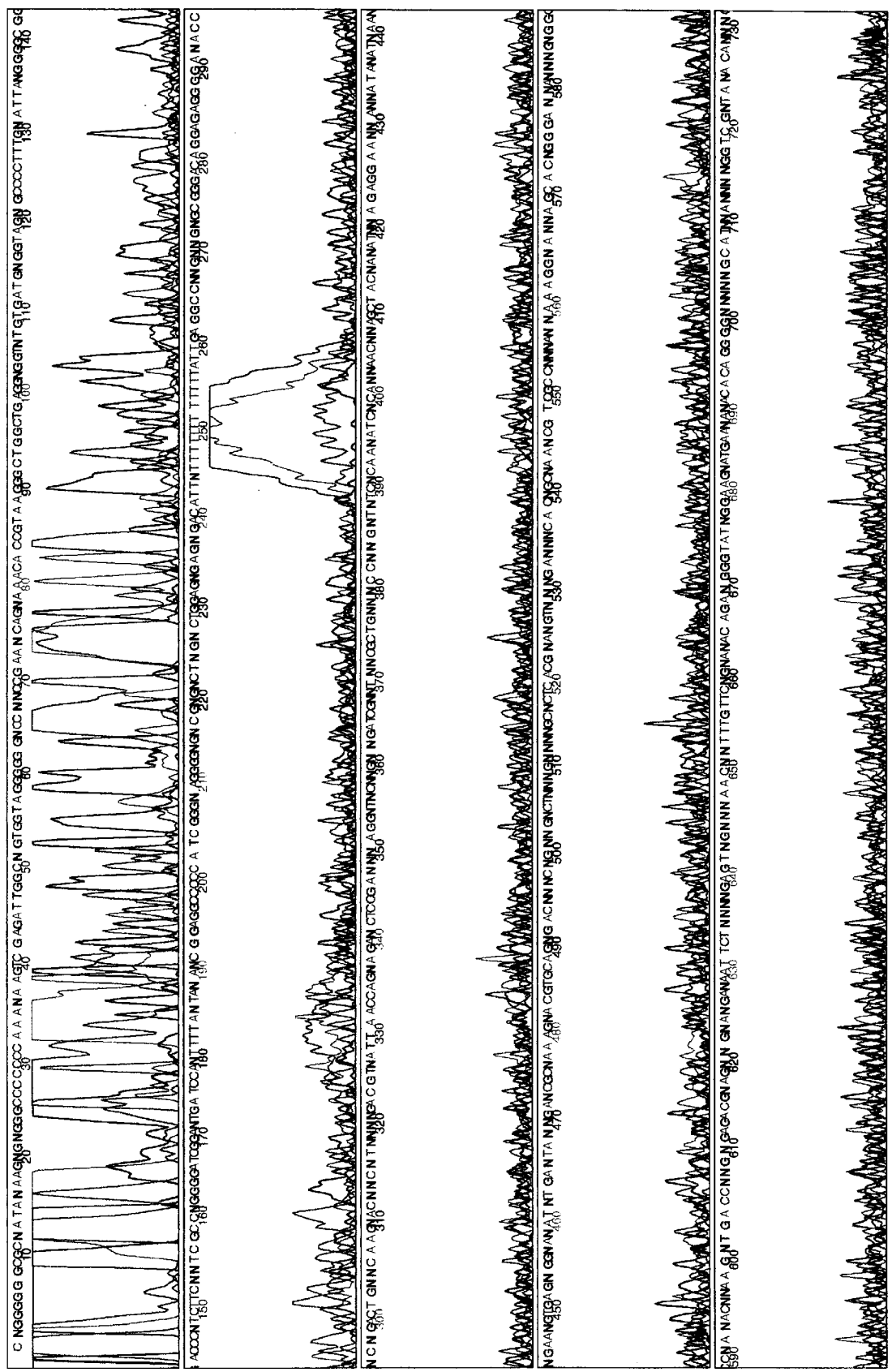
FIGS. 5a and 5b are sequencing readouts of cycle sequencing in accordance with this invention, obtained using Sequitherm® DNA polymerase and the pS71 JB2/primer 4612 template/primer pair at elongation temperatures of 72° C. (5a) and 60° C. (5b).
Figure 5B:
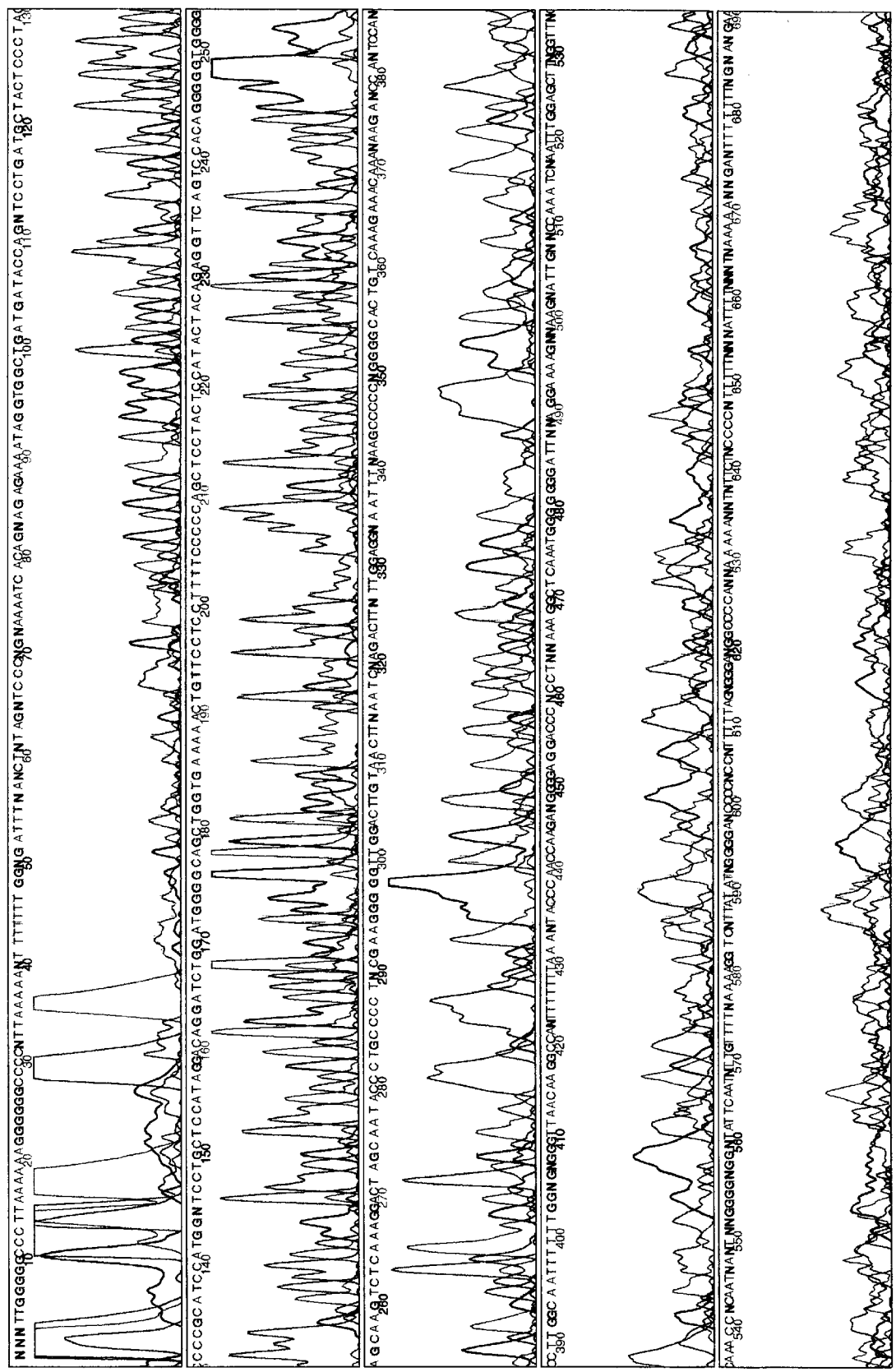

FIGS. 5a and 5b

Standard Sequitherm® Cycle Sequencing Using the pS71JB2/primer 4612 Template-primer Pair at Elongation Temperatures of (a) 72° C. and (b) 60° C.

Standard Sequitherm® cycle sequencing using the pS71JB2/primer 4612 template-primer pair at elongation temperatures of (a) 72° C. and (b) 60° C. Both reactions were prepared according to the worked out standard protocol (0.5 μg of template, 10 pmoles primer, ½ ABI premix, 0.5 μl each of 500 μM dITP/dATP/dTTP/dCTP/100 μM dGTP, 1 μl 30 mM $MgCl_2$, 2.5 U Sequitherm® DNA polymerase, water up to a final volume of 21 μl) FIG. 5a) shows the result of the reaction using the SeqT580 PCR protocol for 2 minutes at 72° C.; FIG. 5b) shows the result of the reaction using the protocol suggested by ABI at a chain elongation temperature of 60° C. for 4 minutes (25 cycles 15 sec 95° C./15 sec 50° C./ 4 min 60° C.).

Figure 6A:
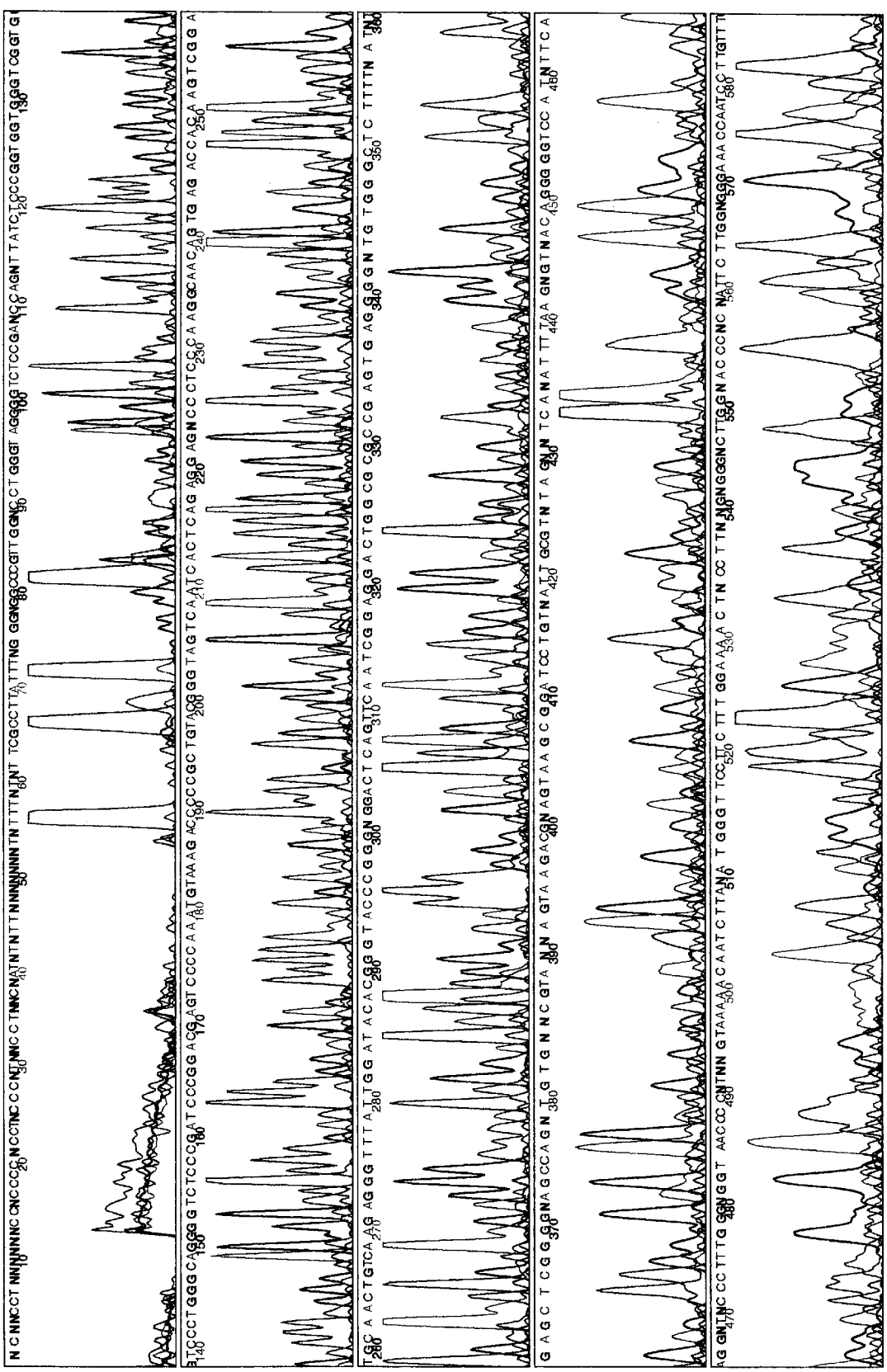
FIGS. 6a, 6b, and 6c are sequencing readouts of cycle sequencing in accordance with this invention, obtained using other template/primer pairs with annealing for 30 sec at 45° C. (6a), employing a 60° C. step prior to elongation (6b), and with the addition of spermidine (6c).
Figure 6B:
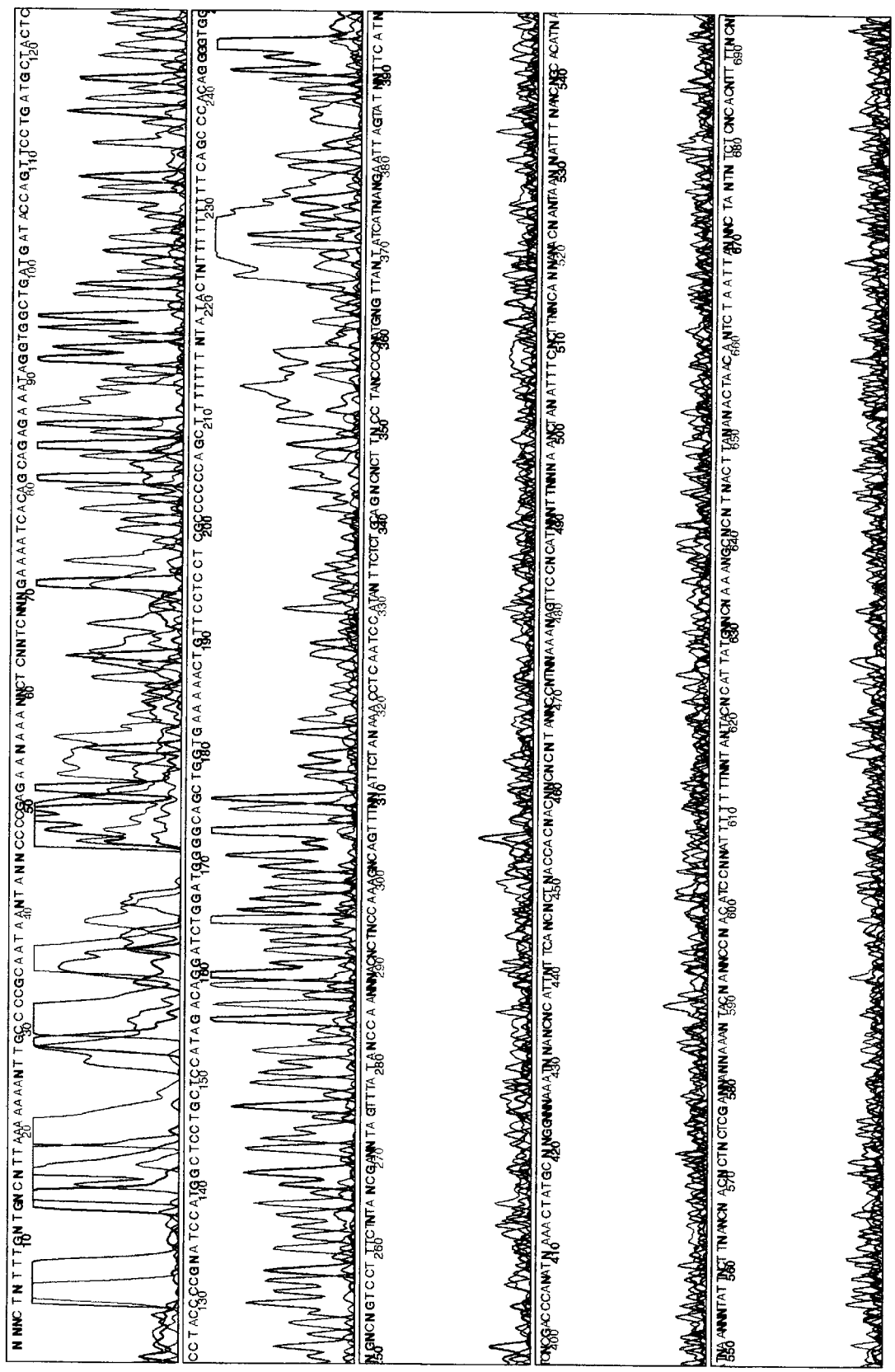
Figure 6C:
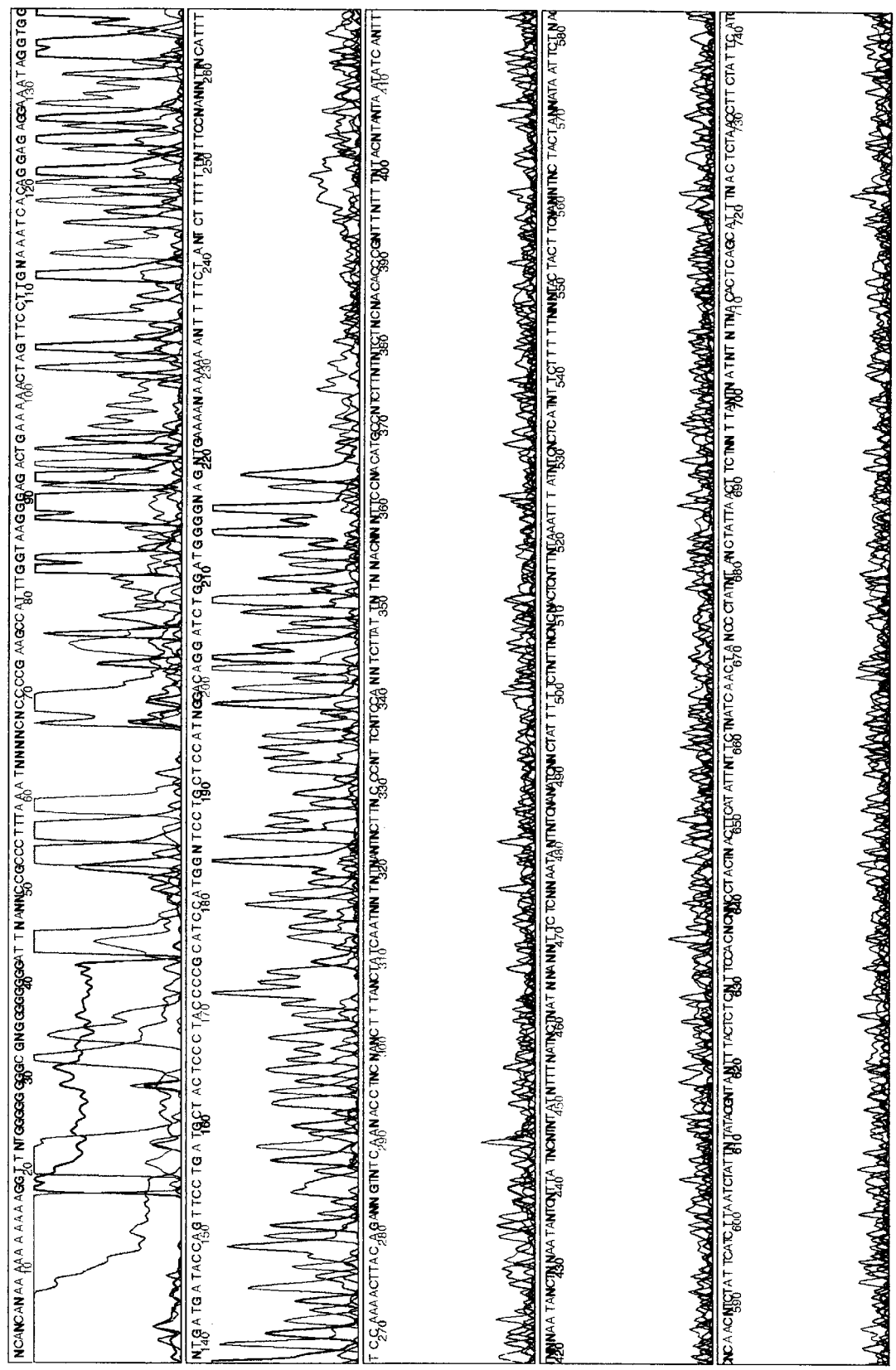

FIGS. 6a, 6b, and 6c

Parameters for Application of the Sequencing Protocols to Other Primer/Template Pairs by Adjusting the Transition From Annealing Temperature to Chain Elongation Temperature a) Longer annealing periods at lower temperatures. Adapting the standard protocol as described for example in FIG. 5 the temperature and the period of the primer annealing step were altered from 15 sec at 50° C. to 30 sec at 45° C.

b) employing a 60° C. step prior to elongation. To slow down the transition from annealing to chain elongation an intervening step of 10 sec 60° C. was employed while all other parameters were kept.

c) Addition of spermidine. In contrast to the standard protocol 1/10 vol of 30 mM spermidine was added to the reaction sample to support the primer/template interaction. Cycle Sequencing at Chain Elongation Temperatures of More Than 60° C.

I. Establishment of a Basic Protocol

In the initial experiments Sequitherm® DNA polymerase was tested for its requirement for magnesium ions to incorporate any dye terminators at all at the temperature of 60° C. usually employed if this polymerase was combined with ABI premix. It is known that magnesium ions are essential for DNA polymerases. For this purpose the following sequencing protocol by ABI was carried out and modified as follows:

Per 21 μl final volume are combined:

9 μl of ABI premix (4 μl 5×TACS buffer/1 μl each of ABI dNTP mix, dyeA, G, C, T)

10 pmoles of primer template DNA (1 μg plasmid, <0.5 μg PCR products)

0.5 μl Sequitherm® DNA polymerase were used instead of 0.25 μl of AmpliTaq® DNA polymerase.

Water ad 20 oder 21 μl

PCR cycle in PE 9600 PCR device without oil:

| Denaturation | 96° C. | 15s |
| Annealing | 50° C. | 15s |
| Chain elongation | 60° C. | 4 min. |
| 25 cycles. | | |

Then, the reaction sample was purified by phenol extraction or CTAB precipitation.

However, the protocol described above gave only insufficient results.

In contrast to the above protocol we now added different concentrations of magnesium chloride. At the same time the 10×Sequitherm® reaction buffer was tested together with the dye terminators and nucleotides of the ABI kit. Randomly selected plasmid templates, pS71JB1 and pS71JB2 containing portions of the S71 locus, as well as a synthetically prepared 22mer "β-gal forward" (CAGCTATGACCATGATTACGCC(SEQ ID NO:1), melting temperature of 53.9° C.) useful as sequencing primer for vetors on the basis of pUC were selected as model systems.

In these basic experiments, the addition of 1 μl of 30 mM magnesium chloride to the ABI premix (in terms of final concentrations: 3.43 mM $MgCl_2$) has been found to enable the incorporation of dye terminators at a chain elongation temperature of 60° C. if Sequitherm® DNA polymerase was used. These experiments were repeated for 65° C. and 70° C.; however at a chain elongation temperature of more than 60° C. an increase in premature chain termination was observed. The "excessive, cut off" peaks observed hereby may be due to a large amount of template, an unsuitable dNTP/terminator ratio and/or an unsuitable PCR cycle. By using half of the amount of template (0.5 μg of plasmide template) in combination with ½, 1/3 or even ¼ of the dye terminators principally similar results were obtained. Eventually stable experiments were achieved by titration of the dNTP/dye terminator ratio thus finding that this ratio changes with the duration of chain elongation. The PCR cycle used in subsequent experiments was named SeqT580 and consists of 5 cycles of 95° C.-15 sec/50° C.-15 sec/80° C.-7 sec/30 cycles at 95° C.-15 sec/50° C.-15 sec/70° C.-2 min. For convenience at this point we did not titrate the concentration of each dye terminator individually but the whole ABI premix. To compensate for this 5 cycles of 7 seconds at a chain elongation temperature of 80° C. were performed to reduce the still high incorporation of the very high concentrated dyeT and dyec terminators.

Because of these preliminary experiments the following basic protocol was established which was used for further optimizations:

The following components were combined to a final volume of 21 μl and subjected to the above PCR cycle:

0.5 μg of plasmid DNA as template (most conveniently resuspended in water);

10 pmoles of primer;

4.5 μl ABI premix (2 μl 5×TACS buffer, 0.5 μl each of dyes ddA/T/G/C, 0.5 μl ABI dNTP mix containing 750 μM dITP and 150μM each of dATP, dTTP, dGTP and dCTP);

0.5 μl 500 μM each of dITP/dATP/dTTP/dCTP/100 μM dGTP;

1 μl 30 M $MgCl_2$;

0.5 μl Sequitherm® DNA polymerase (5U) or another thermostable DNA polymerase;

$dH_2O$ ad 21 μl.

PCR cycle SeqT580—as described above.

| ABI premix: | 5xTACS buffer: |
|---|---|
| 1 μl ddA* | 400 mM Tris-HCl |
| 1 μl ddG* | 10 mM $MgCl_2$ |
| 1 μl ddC* | 100 mM $(NH_4)_2SO_4$, pH 9.0 |
| 1 μl ddT* | |
| 1 μl dNTP mix | |
| 4 μl 5xTACS buffer | |

After adjustment of the concentration of magnesium ions a cycle sequencing with dye terminators using Sequitherm®

DNA polymerase could be performed according to the invention also at a chain elongation temperature of more than 60° C. The reaction conditions may be optimized by routine experimentation in a manner that the amount of template and concentration of dye terminators generally used may be reduced to one half. By reduction of the amount of dye terminators a rapid purification by CTAB becomes possible.

II. Optimization of Process Parameters

Figure 2:
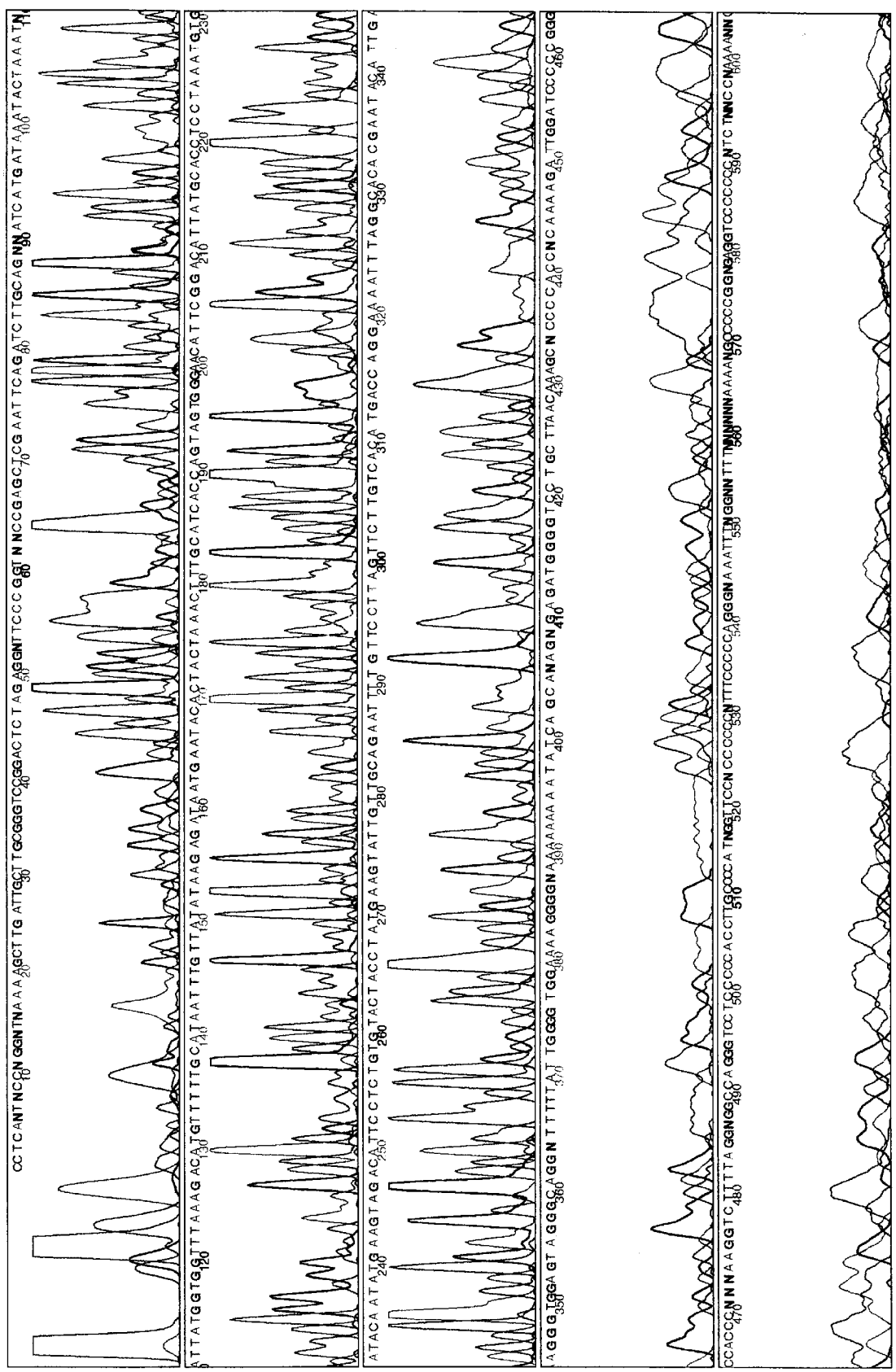
FIG. 2 is a sequencing readout of cycle sequencing in accordance with this invention, obtained using Tth DNA polymerase.

The following parameters were systematically tested for their importance for the reaction procedure: pS71JB1/β-gal forward template/primer pair for Sequitherm® and in part also for Tth and AmpliTaq® DNA polymerases: TACS, MgCl$_2$, DNTP and dye terminator requirements. The results of optimized protocols for Sequitherm® and Tth DNA polymerases are depicted in FIGS. 1 and 2, respectively.

TACS Requirement

Starting from the basic protocol described, i.e. with unchanged PCR cycle, dye terminators, dNTPs and Mg$^{2+}$ concentration, different concentrations of 5×XTACS buffer from ABI were tested: a series of 0.5, 2, 3, 4, 6, 7 μl of TACS at a chain elongation temperature of 70° C. for Sequitherm® DNA polymerase, a series of 0.5, 1, 2, 4, 7 μl of TACS at a chain elongation temperature of 72° C. for Tth DNA polymerase per final volume of 21 μl (in concentrations of 0.125×, 0.5×, 0.75×, 1×, 1.5× or 1.75×, respectively). Best results were obtained for Sequitherm DNA polymerase between 1 and 5 μl of 5×TACS buffer; in contrast Tth DNA polymerase was functional without obvious differences over the whole range of TACS concentrations.

In conclusion under the given experimental conditions both DNA polymerases tolerate a relatively broad range of 5×TACS buffer.

Dye Terminators

In this experimental series the amount of dye terminators was determined which is necessary to obtain a satisfactory sequence. The experiments were performed using Sequitherm® DNA polymerase. At first ½, 1/3 and ¼ of ABI premix were used in the basic protocol described above. A legible sequence was obtained even with ¼ of the premix. Surprisingly, the C and T peaks—the corresponding dye terminators of which are highly concentrated in the ABI premix—still were "excessive and cut off" indicating that the concentration was too high. Therefore, the experiments were carried out at a higher dNPT concentration (1 μl ABI premix plus 0.5 nM dITP/dATP/dCTP/dTTP/0.1 mM dGTP) and with additions of 0.5 and 2 μl of 5×TACS buffer and only 25% of either dyeT, dyec terminators or both terminators together. Very good results could be obtained with a reduced dyec concentration. In contrast without addition of more nucleotides an only indifferent sequence quality was achieved even in the case where the reduced amount of both dyec and dyeT was employed. Half the amount of ABI premix was determined to be a standard value.

In conclusion the dye terminator concentrations for both DNA polymerases thus may be drastically reduced if the dNTP concentration and the PCR cycle are made consistent with each other.

Nucleotide Requirement

The following experiments were carried out with Sequitherm® and Tth DNA polymerases. On the basis of the protocol described above sequences with more than 500 bases were obtained if 1 μl ABI dNTP mix (0.75 mM dITP, 0.15 mM each of dATP/dTTP/dCTP)/0.1 1 μl 6 mM dITP/0.5 mM dATP/dTTP/dCTP/0.1 mM dGTP together with 0.5 μl each of dyeAGT/0.25 μl dyec were added. Still very long sequences were achieved if 0.5 μl of the latter nucleotide mixture were employed where, however, at about the first 50 bases the G termination was insufficient while with 1 μl no sequence ladder was obtained. (The respective concentrations for the first series of experiments are about 64 μM for dITP/17 μM dATP/dCTP/dTTP/0.48 μM dGTP; for the second series of experiments 178.5 μM for dITP/54.75 μM for dATP/dCTP/dTTP/2.4 μM dGTP; and for the third series of experiments 321.4 μM for dITP/102.3 μM for dATP/dCTP/dTTP/4.8 μM dGTP).

In contrast to the basic protocol described above for Tth DNA polymerase 1 μl of ABI DNTP mix was tested with different amounts (1, 2, and 5 μl) of 1) 0.5 mM dITP/dATP/dTTP/dCTP (final concentrations of about 1.59 μM dITP/30.9 μM dATP/dTTP/dCTP); 2) 93.3 μM dITP/64.75 μM dATP/dTTP/dCTP; 3) 154.7 μM dITP/126.1 μM dATP/dTTP/dCTP in 4 μl of 5×TACS buffer. Using the latter two concentrations sequences with up to 400 bases were obtained. Chain lengths of more than 500 bases were obtained if 1 or 2 μl of a dNTP mixture were added consisting of 0.5 mM dITP/dATP/dCTP/0.1 mM dGTP (final concentrations of dGTP of 4.8, 9.6 or 24 μM, respectively).

In conclusion the adjustment of the dNTP/dyeddNTP ratio gave sequence lengths which were such long that the limit of resolution of the 6% polyacrylamide gels used was reached. In general DNTP mixtures using dITP for signal compression in polyacrylamide gels achieved better results than the uniformly concentrated mixtures containing 7-deaza dGTP.

Magnesium Requirement

The Mg$^{2+}$ requirement was systematically tested for Sequitherm® DNA polymerase. 0.5, 1, 2, 3, 5 and 10 μl 30 MM MgCl$_2$ were added while the remaining basic protocol was unchanged. Best results were obtained in a range of 1–5 μl 30 mM MgCl$_2$ while at an addition of 0.5 μl 30 mM MgCl$_2$ only a slight deterioration was obtained. For Tth polymerase the reaction was successful even in experiments with 1 and 10 μl 30 mM MgCl$_2$ and even without any MgCl$_2$.

In conclusion under the reaction conditions given both polymerases tolerate broad concentrations of magnesium chloride. For Sequitherm® DNA polymerase the optimum is at about 2.5 mM, for AmpliTaq® and Tth DNA polymerases at <2 mM MgCl$_2$.

Cycle Conditions With Different Parameters

In an experiment different parameters were altered with unchanged concentration of magnesium ions. A chain elongation time of only 1 min gave unsatisfactory results particularly if a series of 1, 2, 3 μl of TACS was tested with the addition of 1 μl ABI nucleotide mix or 1 μl 15 μM dNTPs. If the chain elongation temperature was extended to 90 seconds clear effects were observed both at different amounts of TACS added and in the addition of dNTPs (1 μl ABI DNTP mix, final concentrations 35.71 μM dITP/7.14 μM dATP/dTTP/dCTP). Eventually dramatic differences were observed if the Sequitherm® DNA polymerase was tested with the "long sequence" DNTP concentration described above (1 μl ABI dNTPs plus 0.1 μl 6 mM dITP/0.5 mM dATP/dTTP/dCTP/0.1 mM dGTP) in amplification cycles having an elongation time of 2 min at 72° C. as compared to 3 min at 70° C. In the first case sequence ladders of more than 500 bases could be obtained while in the second case only 200 bases were achieved emphasizing the relationship between the PCR cycle and the concentrations of dNTPs. Furthermore for Tth DNA polymerase with 2 μl 0.5 mM dITP/dATP/dTTP/dCTP/0.1 mM dGTP (final concentrations of 57.6 μM dATP/dTTP/dCTP/9.6 μM dGTP) even better results were obtained (sequence length of >500 bases) at a chain elongation time of 2 minutes at 72° C. as compared to 3 minutes at 70° C.

These experiments clearly demonstrate that in none of the case the polymerases achieve the "standard rate" of the PCR of 1 kb per minute in a cycle sequencing protocol using dye terminators. It is known from PCR that the concentration of magnesium ions and the total DNTP concentration are related to each other: it could be shown herein that there is a further relationship between the chain elongation time and the dye terminator/dNTP ratio.

Chain Elongation Temperature

In addition, dye terminators were found to be very well incorporated if the basic protocol described above was carried out at a chain elongation temperature of 72° C. Sequitherm® polymerase and particularly Tth DNA polymerase worked very well also at 75° C. However, clearly inferior results were obtained at a chain elongation temperature of 80° C.

Thus, in cycle sequencing using dye terminators the extremely thermophilic DNA polymerases show similar temperature optima as in PCR but without attaining the reaction rate of classical PCR.

Addition of "Catalytic Amounts" of Other DNA Polymerases Some of Which Have Proof-reading Activity It is known for "long PCRs" that premature chain termination is caused by incorrectly incorporated nucleotides. Therefore, the addition of a "catalytically" active amount of DNA polymerases having a slight (AmpliTaq®) or a completely functional 3', 5'-exonuclease activity was tested. In experiments using an elongation time of only one minute "catalytic" amounts of 0.5 U Pfu or 0.5 U AmpliTaq® resulted in better sequences than 1/1 mixtures. Using enzyme mixtures the sequencing protocols could be optimized.

Additives

The detergents Tween® 20 and TritonX® and the "co-solvents" DMSO and glycerol were used to improve the PCR and DNA sequencing which in part has an effect on thermal stability of the template DNA double helix. The additive additions used to improve DNA sequencing with AmpliTaq® DNA polymerase at 60° C. were also tested for Sequitherm® and Tth DNA polymerases at 72° C. The results show that the additives typically employed are unable to achieve a further improvement of the sequencing result with the Sequitherm® and Tth DNA polymerases for the primer/template pair used.

III. Use of Other Extremely Thermophilic DNA Polymerases at Chain Elongation Temperatures of More Than 60° C.

In the following experiments we examined whether other extremely thermophilic DNA polymerases besides Sequitherm® DNA polymerase are useful in cycle sequencing with dye dideoxy terminators at chain elongation temperatures in excess of 60° C.

Using the basic sequencing protocol described above (PCR cycle SeqT580, pS71JB1 as template, β-gal forward as primer) the following extremely thermophilic DNA poylmerases were tested for their ability to incorporate dye terminators at a chain elongation temperature of 70° C. with and without addition of 1 μl 30 mM $MgCl_2$. The following extremely thermophilic DNA polymerases were found to work upon addition of 1 μl 30 mM $MgCl_2$ at a chain elongation temperature of 70° C.: Sequitherm (Epicentre), Tth (Epicentre, Boehringer), TaqPlus (Stratagene), Expand HIFI (Boehringer), Tfl (Epicentre), Replitherm (Epicentre), and Goldstar (Eurogentec). Despite of inferior overall results, also Deep Vent, Vent exo⁻ and 9°N DNA polymerases by the addition of $MgCl_2$ are in principle useful at an elongation temperature of 70° C. Surprisingly, the following extremely thermophilic DNA polymerases were found to be useful at chain elongation temperatures of >60° C. even without addition of 1 μl 30 μM $MgCl_2$, i.e. with the amount of $MgCl_2$ already used in the starting protocol: Goldstar®, Boehringer HIFI, TaqPlus®, Tth, Tfl, and AmpliTaq® showing that generally many DNA polymerases from extremely thermophilic organisms are able to incorporate dye terminators in cycle sequencing.

Thus, it has been found for the primer/template pair examined that all of the DNA polymerases tested are capable of incorporating dye terminators at a chain elongation temperature of 70° C. These findings are presented illustratively with respect to the Replitherm® and Tfl DNA polymerases in FIGS. 3 and 4, respectively.

IV. Applicability of the Results to Other Primer/template Pairs

To examine whether the use of extremely thermophilic DNA polymerases in cycle sequencing with dye terminators at temperatures in excess of 60° C. is also possible with other primer-template pairs, experiments were conducted with pS71JB2 and the β-gal for primer and with pS71JB4 and the S71-specific primer 4935. It was found that particularly the transition from primer annealing to chain elongation is critical for the method according to the invention. I.e. the addition of spermidine had a positive effect on the method according to the invention.

Thus, extremely thermophilic DNA polymerases have been found according to the invention to be useful in cycle sequencing with dye terminators also at chain elongation temperatures of more than 60° C., particularly at temperatures in the range of 70° C. to 75° C., optimally at 72° C. Particularly preferred the Sequitherm® and Tth DNA polymerases are employed according to the invention. However, also other extremely thermophilic DNA polymerases known per se may be employed. Depending on the primer/template pair and the DNA polymerase used the experimental conditions for cycle sequencing using dye terminators may be optimized in a conventional manner. These are routine modifications of the cycle sequencing procedure using dye terminators known to those skilled in the art wherein according to the invention temperatures of more than 60° C. are employed for chain elongation. In particular, in the optimization of cycle sequencing the following conditions should be adjusted with respect to each other and optimized depending on the primer-template pair and the DNA polymerase used:

concentration of magnesium ions;

buffer composition;

substitution of magnesium ions by other metal ions;

concentration of nucleotides;

concentration of extremely thermophilic DNA polymerase;

PCR conditions, particularly those for primer annealing and the transistion conditions between primer annealing temperature and chain elongation temperature which always is in excess of 60° C., preferably in the optimal range of 70–75° C.;

appropriate selection of the additives for stimulation of primer annealing, chain elongation and enzyme activity for example by addition of PEG and stabilizers of the DNA structure such as spermidine.

The present invention shows for the first time that extremely thermostable DNA polymerases are generally capable of incorporating modified dideoxy nucleotides such as dye terminators at temperatures >60° C. This finding has far-reaching consequences for the optimization of sequencing and amplification protocols intending to use such nucleotide analogs. Thus, the results obtained clearly show that the applicability of previous protocols which are only capable of working at 60° C. have to be optimized by adjusting the reaction conditions to the respective primer/ template pair used. Thus the experiments conducted with pS71JB2/primer 4612 at 60° C. and 72° C. clearly demonstrate that the transition from annealing to chain elongation is an important point.

This finding is supported by the fact that modifications of the PCR cycle to lower annealing temperatures (450C instead of 50° C.) with extended annealing periods (30 sec instead of 15 sec) as well as employing an intervening step of 10 sec at 60° C. between annealing at 50° C. and extension at 72° C. lead to dramatically improved results. If the primer/template interaction is promoted by additives such as spermidine similarly strongly improved results are obtained as compared to the 72° C. basic protocol. A further novelty of the present invention is particularly the use of spermidine. It has been for example employed to promote restriction digestions and DNA-protein interactions in gelshift experiments but never as an adjuvant for DNA sequencing with dye terminators.

A use of this research has in part already brought about very good results in the adaption of the Thermosequenase® DNA polymerase protocol to the novel cycle sequencing kit of ABI company supplied with strongly reduced dye terminator concentrations using AmpliTaqFS®. By the addition of additives such as spermidine it is even possible to obtain sequences using AmpliTaq® DNA polymerase which has been "replaced" by AmpliTaq FS® DNA polymerase. Furthermore, for the Tth® and Sequitherm® DNA polymerases conveniently applicable 60° C. protocols could be established at a reduced dye terminator requirement as compared to AmpliTaq® by simple addition of magnesium; as already indicated above the reaction conditions for AmpliTaq® DNA polymerase might still be strongly improved.

In conclusion the invention describes not only a novel use of extremely thermophilic DNA polymerases but also parameters and additives for the establishment and optimization of protocols using extremely thermophilic DNA polymerases and substituted nucleotides. A finding which is particularly important according to the invention and critical for the practice of the invention is that the following parameters must be adjusted in relation to each other to perform cycle sequencing of DNA with marker-substituted dideoxynucleotides at a temperature >60° C. These parameters are:

reaction buffer;

deoxynucleotides;

marker-substituted dideoxynucleotides;

primer and template DNAs;

additives;

ramping time between the individual temperature stages in dependence on the DNA polymerase, template/ primer pair and reaction buffer used.

What is claimed is:

1. In a method for cycle sequencing of DNA in the form a 1-lane technique using dideoxynucleotides labeled with a dye as a marker, wherein sequence ladders of more than 500 bases are obtained, comprising the steps of:

a) mixing at least a reaction buffer, deoxynucleotides, the marker-labeled dideoxynucleotides, primers and double stranded DNA template, water and optionally further additives and adjusting the concentration thereof in relationship to each other;

b) adding at least one extremely thermostable DNA polymerase, c) performing PCR sequencing cycles comprising the steps of:

denaturing the template DNA at an appropriate temperature;

annealing the primer at an appropriate temperature;

chain elongation at an appropriate temperature; and adjusting the ramping time between the individual temperature stages in dependence on the DNA polymerase, template/primer pair and reaction buffer used;

d) purifying the reaction sample; and e) separating the DNA chains and detecting to determine the DNA sequence; the improvement comprising:

(i) in step c) performing the chain elongation at a temperature of 65° C. to 75° C.;

(ii) depending on the primer/template pair and DNA polymerase used, adjusting the following conditions in relationship to each other to enable chain elongation in a temperature range of 65° C. to 75° C.:
concentration of metal ions;
concentration of nucleotides;
concentration of DNA polymerase; and
the conditions for primer annealing as well as conditions for transition from primer annealing to chain elongation temperature; and (iii) adding additives for stimulation of primer annealing, chain elongation and DNA polymerase activity.

2. Method according to claim 1, wherein the buffer contains alkaline metal ions or alkaline earth metal ions.

3. Method according to claim 2, wherein magnesium ions are used as said alkaline earth metal ions.

4. Method according to claim 1, wherein in step c) the chain elongation is performed at a temperature in the range of 68° C. to 73° C.

5. Method according to claim 1, wherein in step c) the chain elongation is performed at a temperature in the range of 70° C. to 72° C.

6. Method according to claim 1, further comprising adding polyethylene glycol, stabilizers of DNA structure, or both, in step a).

7. Method according to claim 1, wherein dideoxynucleotides labeled with a fluorescent dye are used as a marker.

8. Method according to claim 1, wherein spermidine is added as a stabilizer of DNA structure.

* * * * *